United States Patent [19]

Rabinowitz

[11] Patent Number: 4,653,480
[45] Date of Patent: Mar. 31, 1987

[54] GUM MASSAGER
[75] Inventor: Lewis Rabinowitz, Glendale, Ariz.
[73] Assignee: Arnell Inc., Glendale, Ariz.
[21] Appl. No.: 766,536
[22] Filed: Aug. 19, 1985

Related U.S. Application Data

[63] Continuation-in-part of Ser. No. 391,530, Jun. 24, 1982, Pat. No. 4,535,761.

[51] Int. Cl.⁴ .............................................. A61H 7/00
[52] U.S. Cl. ................................................ 128/62 A
[58] Field of Search ....................... 128/62 A; 15/110; 2/421; 132/89; D4/24; D28/64

[56] References Cited

U.S. PATENT DOCUMENTS

| | | | |
|---|---|---|---|
| 2,042,239 | 5/1936 | Planding | 15/110 |
| 3,050,072 | 8/1962 | Diener | 15/110 |
| 3,368,553 | 2/1968 | Kirby | 128/62 A |
| 3,480,981 | 12/1969 | Murov et al. | 128/62 A |

Primary Examiner—Robert Peshock
Attorney, Agent, or Firm—Herbert E. Haynes, Jr.

[57] ABSTRACT

A device for massaging gums having a handle portion arranged for manually manipulating the device in order to impart a swivel-like movement to a gum massaging element that is mounted on the handle portion and configured for insertion between adjacent teeth of a user of the device. A universal joint coupling structure interconnects the handle and the massaging element to allow a free changing of the angular relationship therebetween to provide the swivel-like movement of the gum massaging element.

18 Claims, 4 Drawing Figures

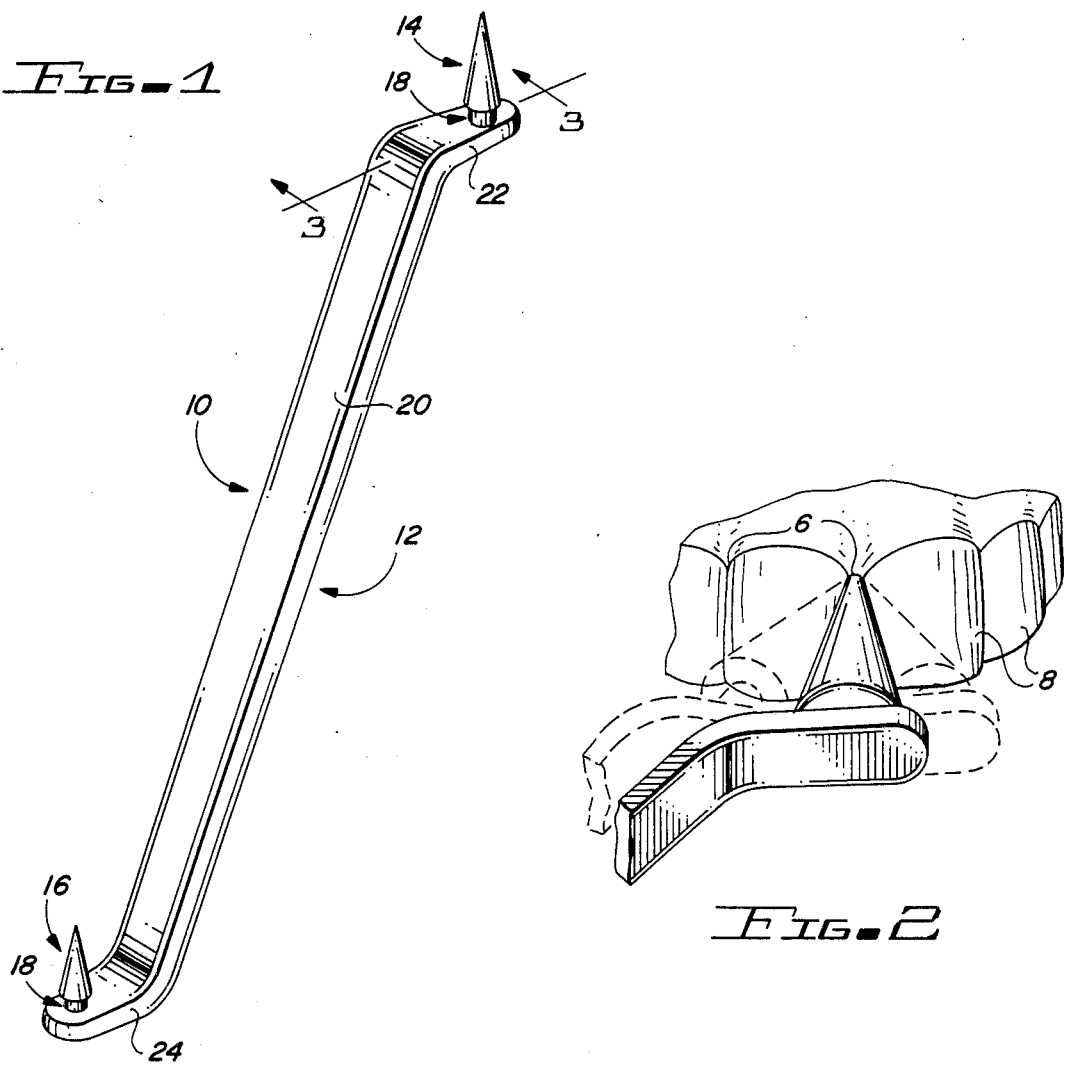
Fig-1
Fig-2
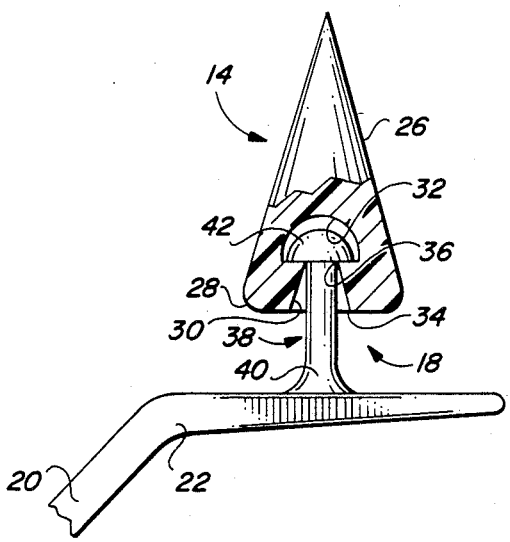
Fig-3
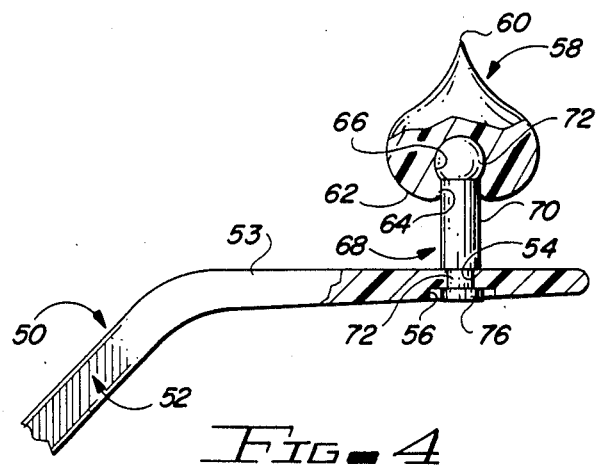
Fig-4

GUM MASSAGER

CROSS REFERENCE TO RELATED APPLICATION

This application is a continuation-in-part of a copending prior U.S. patent application Ser. No. of 391,530, filed June 24, 1982 and now Pat. No. 4,535,761 issued Aug. 20, 1985, for GUM MASSAGER by the same inventor.

BACKGROUND OF THE INVENTION

1. Field of the Invention

This invention relates generally to dental appliances, and more particularly to apparatus for massaging areas of a user's gums located between the user's teeth.

2. Description of the Prior Art

The desirability of massaging ones gums has long been known. U.S. Pat. No. 1,086,936, issued Feb. 10, 1914, to M. Pounder, et al, discloses a dental massage implement having a generally conoidal massaging head rotatably mounted on one end of a manipulating handle. This known massaging head is generally formed from a resilient material such as a soft rubber, and advantageously is provided with longitudinally extending ribs arranged for producing a desired vibratory effect. A basic disadvantage with this prior device is that a conoidal configuration does not properly fit the outer surfaces of gums being massaged.

Another known gum massager device is disclosed in U.S. Pat. No. 2,091,511, issued on Aug. 31, 1937, to B. London. This known device employs a pair of massager tips fabricated from rubber and disposed at respective free ends of similar spring arms projecting from a common handle. The massager tips each are in the configuration of a conventional door knob, and the like, and once again do not readily conform to the surface of gums being massaged.

U.S. Pat. No. 1,533,528, issued Apr. 14, 1925, to J. A. Weaver, and U.S. Pat. No. 2,074,735, issued Mar. 23, 1937, to J. Puttcamp, disclose devices intended to be used for massaging ones back and ones face, respectively. The latter is of a conoidal configuration as discussed above, while the former employs a symmetrical, grooved roller, the hyperboloid configuration of this roller, while more suitable for gum massaging than the aforementioned conoidal configuration, still is not optimumly suited for gum massaging applications.

In addition to massaging the outer and inner surfaces of ones gums, it is desirable to massage the areas of gums disposed between ones teeth and the above described prior art structures do not make provisions for such massaging. Although it is known to provide flexible toothpicks, as set forth in U.S. Pat. No. 516,409, issued on Mar. 13, 1894, to C. C. Southwell, such appliances are suitble only for their intended use, that of cleaning between adjacent teeth, and do not provide the requisite vibratory, or swivel-like, action desired for gum massaging operations. Further, U.S. Pat. No. 710,498 issued Oct. 7, 1902, to D. McClain, discloses a toothpick having a rigid point set at a right angle to the shank thereof, which arrangement is also capable only of cleaning between adjacent teeth and not massaging the associated gum area. The same can be said for the toothpick disclosed in U.S. Pat. No. 1,654,230, issued Dec. 27, 1927, to H. Zimmerman, and to the rigid hook forming the rear end of a handle of a toothbrush as disclosed in U.S. Pat. No. 1,784,986, issued Dec. 16, 1930 to S. Eisenberg.

U.S. Pat. No. 4,205,664, issued June 3, 1980 to M. O. Baccialon, discloses a tooth and gum massaging implement having a pair of rigid massaging elements of different configurations extending from opposed ends of a longitudinally extending handle portion. Once again, however, the massaging elements are rigidly attached to the associated handle, making it impossible to obtain a desired vibratory swivel-like action against gums being massaged.

U.S. Pat. No. 3,985,147, issued Oct. 23, 1976 to C. M. Ricketts, et al, discloses a dental implement for removing stains from teeth in which a pick and hole are rigidly disposed on one end of a longitudinally extending handle, at the other longitudinal end of which is provided a disc. As with the devices described above, this appliance is intended only for cleaning teeth, and is not capable of achieving a vibratory swivel-like action desired for massaging gums.

SUMMARY OF THE INVENTION

It is an object of the present invention to provide a new and improved gum massaging device capable of providing vibratory swivel-like motion when massaging gum areas located between adjacent teeth.

It is another object of the present invention to provide a new and improved gum massaging device of the above described character which is capable of massaging gum areas between adjacent teeth in all parts of a user's mouth.

Still another object of the present invention is to provide a new and improved gum massaging device of the above described type which is inexpensive to manufacture, simple to use, and is beneficial for promoting healthy gums of a user.

These and other objects are achieved according to the present invention by providing a gum massaging device comprising a handle arranged for manipulating the apparatus and having attached thereto a substantially rigid massaging element for insertion between the teeth of a user of the device. The massaging element is articulated to the handle by a universal coupling joint which permits a free swivel-like motion of the massaging element relative to the handle part.

The massaging element preferably includes a tapered body constructed from a soft yet rigid material selected for preventing damage to a user's gums. In the preferred embodiment of the present invention, the handle part and the massaging part are formed as separate pieces which are interconnected by cooperating elements formed on the handle and on the massaging element with those cooperating elements interacting to provide the universal coupling joint.

In a second embodiment, the handle part and the massaging part are formed as separate pieces as in the preferred embodiment and are interconnected by a separate flexible member which provides the universal coupling joint.

In both embodiments of the present invention, the handle is of rigid material and includes a straight portion with an offset end portion, and the body of the massaging element is of generally conical configuration and arranged mounted on the offset portion so as to extend substantially normally therefrom. The handle may include a pair of such offset end portions extending in spaced relation from the straight portion so as to form a symmetrical arrangement with each of the offset portions being provided with a respective massaging element, each like the one massaging element and extending codirectionally of each other.

The foregoing and other objects of this invention as well as the invention itself, may be more fully understood when read in conjunction with the following drawings.

BRIEF DESCRIPTION OF THE DRAWINGS

FIG. 1 is a generally perspective view showing the preferred embodiment of the gum massaging device according to the present invention.

FIG. 2 is a fragmentary perspective view showing a portion of a user's teeth with the gum massaging device of the present invention being shown in an operative position relative thereto.

FIG. 3 is an enlarged fragmentary sectional view taken generally along the line 3—3 of FIG. 1.

FIG. 4 is a view similar to FIG. 3 and showing a modification of the device of the present invention.

DESCRIPTION OF THE PREFERRED EMBODIMENTS

Referring more particularly to the drawings, FIGS. 1, 2 and 3 show a gum massaging device, in accordance with the present invention, for massagingly stimulating the gum areas 6 between the teeth 8 of a user, with the preferred embodiment of the device being indicated in its entirety by the reference numeral 10. The device 10 includes a handle means 12 having at least one, and preferably the illustrated two, massaging means 14 and 16 articulated thereto by means of cooperating elements of a universal joint coupling structure 18. The handle means 12 is adapted for manual manipulation of a user so as to impart a vibratory swivel-like, or wiggling, massaging motion to one of the massaging means 14 or 16 when inserted between the user's teeth proximate the gum line.

The handle means 12 includes an elongated straight portion 20 and at least one, and preferably the illustrated pair, of angularly extending, or offset end portions 22 and 24 which terminate the opposed ends of the straight portion. The handle means 12 is molded or otherwise formed of a suitable rigid material such as that from which toothbrush handles are commonly made. As will hereinafter be described in detail, the massaging means 14 and 16 are arranged so as to extend codirectionally and substantially normally from their respective offset end portions 22 and 24 and the angularly extending attitudes of the offset portions 22 and 24 are selected at different angles to facilitate gum massaging in all areas of a user's mouth.

The two illustrated massaging means 14 and 16, their associated and respective cooperating elements of a universal joint-type coupling structures 18, and their respective offset end portions 22 and 24 of the handle means 12 are identical. Therefore, since FIG. 3 illustrates the specific offset portion 22, massaging means 14 and a single one of the cooperating elements of a universal joint-type coupling structure 18, only those parts will be referred to in the folliwing discussion, with it being understood that the following discussion also relates to the other non-specifically discussed parts.

The massaging means 14 includes a generally tapered body portion 26, preferably conical, which is molded or otherwise formed of a soft yet fairly rigid material, such as a natural or synthetic rubber, and which may be similar to materials commonly used for making the massaging tips which are provided on the handle ends of some brands of toothbrushes. When formed of this soft yet fairly rigid material, the conical massaging body 26 will be fairly rigid at the base thereof, but will tend to become somewhat flexible toward its apex. Alternatively, the massaging body portion 26 may be formed of a relatively hard and rigid material with there being a multiplicity of materials suitable for this purpose under the general classification of synthetic resins. For reasons which will hereinafter be described, when formed of this latter type of material, it is preferred that the material be thermoplastic.

The conical body portion 26 of the massaging means 14 has one of the cooperating elements of the universal joint coupling structure 18 formed therein in the form of a socket means. The socket means is in the form of an especially configured blind bore which extends from the base 28 of the body portion 26 toward the apex and includes an inwardly converging throat portion 30 and an enlarged cavity portion 32. The throat portion 30 is in the general form of a truncated cone having the larger diameter opening 34 thereof on the base 28 of the body portion 26 of the massaging means 14 and having the reduced diameter opening 36 in communication with the enlarged cavity portion 32 of the blind bore.

The second one of the cooperating elements of the universal joint coupling structure 18 is in the form of a pedestal means 38 which is molded or otherwise formed on the offset end portion 22 of the handle means 12. The pedestal means 38 includes a shank portion 40 which extends perpendicularly from the offset end portion 22 and has an enlarged head 42 on its extending end. The shank portion 40 is of circular cross section and has a diameter which is sleightly smaller than the reduced diameter opening 36 of the hereinbefore described blind bore provided in the massaging means 14.

As shown, the conical body portion 26 of the massaging means 14 is mounted on the pedestal means 38 so that the enlarged head 42 of the pedestal means 38 is disposed loosely within the cavity portion of the blind bore and the shank portion 40 is disposed substantially axially in the throat portion of the blind bore. In that the enlarged head 40 of the pedestal means is loosely contained in the internal cavity 32 of the blind bore and the diameter of the shank portion 40 is smaller than the reduced diameter opening 36 of the conically configured throat portion 30 of the blind bore, the massaging means 14 may be moved in a swivel-like movement on the pedestal means 38, as indicated in dashed lines in FIG. 2.

When the conical body portion 26 is formed of the rigid yet soft material suggested first above, it may be installed on the pedestal means by simply, pushing it axially onto the pedestal. The natural elasticity of this first suggested material will permit such an installation procedure.

However, the second material hereinbefore suggested may not lend itself to the above described installation technique. For example, the thermoplastic material mentioned above may be selected from the family of thermoplastic polyolefinic elastomers which are available in a wide range of hardnesses and flexibilities. When the selected range of such matetial is such that its elasticity will not allow a push-on type of installation of the massaging means 14 on the pedestal means 38, it may be necessary to use heat for material softening during installation.

To use the gum massage device 10 of the present invention, a user inserts the apex of the massage means 14 between his teeth 8 proximate the gum line 6, and manually manipulates the handle means 12. When used in this manner, the user's teeth form what may be considered a loose fulcrum and gum massaging and stimulating benefits are derived from the swivel-like movement provided at the base of the massaging means 14 by the cooperating elements of the universal joint coupling structure 18 which allows a free changing of the angular relationship between the massaging means 14 and the handle means 12 when the handle means is manually manipulated.

Reference is now made to FIG. 4 wherein a modification of the device of the present invention is shown, with the device being indicated generally by the reference numeral 50.

The gum massaging device 50 includes a handle means 52 which is essentially the same as the hereinbefore described handle means 12 with the exception that its offset end portion 53 is formed with a transverse bore 54 having a countersink 56, rather than being formed with the integral pedestal means 38 of the handle means 12.

The gum massaging device 50 further includes a massaging means 58 which is shown as being of a tear-drop configuration which includes an apex 60 and base 62. It is to be understood that the tear-drop configuration of massaging means 58 and the generally conical configuration of the hereinbefore described massaging means 14 and 16 are interchangeable and functional equivalents of each other. Therefore, the massaging means 14, 16 and 58 may be formed in either of those configurations or in others of the same basic shape.

The massaging means 58, which may be formed of the materials hereinbefore suggested, is provided with a blind bore 64 extending from its base 62 toward its apex 60. The blind bore 64 is of cylindrical configuration and terminates at its inner end in a spherical enlargement 66.

The universal joint coupling structure of this embodiment is in the form of a flexible means 68. The flexible means 68 includes a shank portion 70 having a sphere 72 on one end which is contained in the spherical enlargement 66 provided in the massaging means 58 and thereby attaches massaging means thereto. The opposite end of the flexible means 68 may be attached to the offset end 53 of the handle means 52 in any suitable manner such as by forming an annular groove 74 in spaced relationship with respect to the end of the shank 70 and thereby provide a knob 76 on that end of the shank. The reduced diameter portion of the shank 70 formed by the annular groove 74 extends snugly through the transverse bore 54 and the knob end 76 of the shank is disposed in the countersink portion 56 of the bore.

The flexible means 68 formed of an elastomeric material such as natural or synthetic rubber or any of the hereinbefore discussed synthetic elastomers. Therefore, the flexible means 68 provides the gum massaging device 50 with swivel-like movements of the same type as described above with regard to the device 10.

While the principles of the invention have now been made clear in the illustrated embodiments, there will be immediately obvious to those skilled in the art, many modifications of structure, arrangements, proportions, the elements, materials and components used in the practice of the invention, and otherwise, which are particularly adapted for specific environment and operation requirements without departing from those principles.

For example, the flexible means 68 described above can be formed in other ways such as by embedding a flexible spring-like element (not shown) in a soft non-elastomeric material.

The appended claims are therefore intended to cover and embrace any such modifications within the limits only of the true spirit and scope of the invention.

What I claim is:

1. A device for massaging gums comprising in combination:
   (a) handle means for manipulation of the device;
   (b) a substantially rigid massaging means arranged for insertion between the teeth of a user of the device; and
   (c) cooperating elements of a universal joint coupling structure formed in said massaging means and on said handle means for interconnection thereof so that said massaging means normally extends perpendicularly from said handle means and is freely movable in a swivel-like motion for free changing of the angular relationship between said massaging means and said handle means when said massaging means is inserted between the teeth of a user and upon manipulation of said handle means, said cooperating elements of a universal joint coupling structure including a socket means formed in said massaging means and a pedestal means extending substantially perpendicularly from said handle means said pedestal means having an enlarged head on its distal end which is loosely contained in said socket means, said socket means being larger than said head of said massaging means to allow the swival like motion of said massaging means.

2. A device as claimed in claim 1 wherein said massaging means is of substantially conical configuration defining an apex for insertion between the teeth of a user and a base in which said socket means of said cooperating elements of a universal joint coupling structure is formed.

3. A device as claimed in claim 2 wherein said massaging means is configured to provide said socket means thereof with a throat portion of truncated conical configuration which convergingly extends from the base toward the apex thereof and an enlarged cavity in communication with the inwardly disposed opening of the throat portion.

4. A device as claimed in claim 3 wherein said pedestal means includes a shank portion extending substantially perpendicularly from said handle means through the throat portion of said socket means of said massaging means, said enlarged head of said pedestal portion being in the enlarged cavity of said socket means of said massaging means.

5. A device as claimed in claim 4 wherein said shank portion of said pedestal means is of circular cross section and has a diameter which is slightly smaller than the inwardly disposed opening of the throat portion of said socket means of said massaging means.

6. A device as claimed in claim 1 wherein said massaging means is fabricated of a rigid material.

7. A device as claimed in claim 1 wherein said massaging means is fabricated of a soft yet rigid material selected for preventing damage to a user's gums.

8. A device as claimed in claim 1 wherein said handle means includes a straight portion and at least one offset end portion, said massaging means being mounted on the offset end portion of said handle means by said cooperating elements of a universal joint coupling structure.

9. A device for massaging gums comprising in combination:
   (a) handle means for manipulation of the device;
   (b) a substantially rigid massaging means of substantially conical configuration defining an apex for insertion between the teeth of a user of the device and defining a base; and
   (c) cooperating elements of a universal joint coupling structure formed in said massaging means and on said handle means for interconnection thereof so that said massaging means normally extends perpendicularly from said handle means and is movable in a swivel-like motion for free changing of the angular relationship between said massaging means and said handle means when the apex of said massaging means is inserted between the teeth of a user and upon manipulation of said handle means, said cooperating elements of a universal joint coupling structure including,
   I. said massaging means defining a blind bore having a throat portion of truncated conical configuration convergingly extending from the base toward the apex thereof and an enlarged cavity at the inwardly disposed opening of said throat portion,
   II. a pedestal on said handle means and including a shank portion extending perpendicularly from said handle means through the throat portion of the blind bore defined by said massaging means and an enlarged head on the extending end of said shank and disposed in the enlarged cavity of the bline bore defined by said massaging means.

10. A device as claimed in claim 9 and further comprising:
    (a) said shank portion of said pedestal being of circular cross section and having a diameter proximate its extending end which is sleightly smaller than the inwardly disposed opening of the throat portion of the blind bore defined by said massaging means; and
    (b) said enlarged head of said pedestal being smaller than the enlarged cavity of the blind bore defined by said massaging means for loose containment of said enlarged head within the enlarged cavity of the blind bore of said massaging means.

11. A device as claimed in claim 9 wherein said massaging means is fabricated of a rigid material.

12. A device as claimed in claim 9 wherein said massaging means is fabricated of a soft yet rigid material selected for preventing damage to a user's gums.

13. A device as claimed in claim 9 wherein said handle means includes a straight portion and at least one offset end portion, said massaging means being mounted on the offset end portion of said handle means by said cooperating elements of a universal joint coupling structure.

14. A device for massaging gums comprising in combination:
    (a) handle means for manipulation of the device;
    (b) a substantially rigid massaging means arranged for insertion between the teeth of a user of the device; and
    (c) a universal joint coupling means interconnecting said massaging means and said handle means so that said massaging means normally extends perpendicularly from said handle means and is movable in a swivel-like motion for free changing of the angular relationship between said massaging means and said handle means when said massaging means is inserted between the teeth of a user and upon manipulation of said handle means, said universal joint coupling structure including a flexible shank means which extends from said handle means and has one end which is attached to said massaging means with the other end being attached to said handle means.

15. A device as claimed in claim 14 wherein said massaging means is of a substantially tear-drop like configuration defining an apex for insertion between the teeth of a user.

16. A device as claimed in claim 14 wherein said flexible shank means is elongated and is formed of an elastomeric material.

17. A device as claimed in claim 14 and further comprising:
    (a) said massaging means being of tapered configuration defining a base proximate said handle means and an extending apex for insertion between the teeth or the user, said massaging means having a blind bore formed so as to extend from its base toward its apex and having an enlarged cavity at its innermost end; and
    (b) said flexible shank having an enlargement on the one end thereof which is attached to said massaging means with said enlargement being disposed in the enlarged cavity portion of the blind bore defined by said massaging means.

18. A device as claimed in claim 14 and further comprising:
    (a) said handle means having a transverse bore formed therein with a countersunk portion; and
    (b) said flexible shank means having an annular grooved formed proximate the other end thereof which is attached to said handle means to provide a reduced diameter portion in spaced relationship from that other end and a knob portion at that other end with the reduced diameter portion extending through the transverse bore of said handle means and the knob being disposed in the countersunk portion thereof.

* * * * *